United States Patent

Sato et al.

[11] 4,096,143
[45] Jun. 20, 1978

[54] PROCESS FOR PRODUCING PHTHALAZINONE AND DERIVATIVES OF THE SAME

[75] Inventors: Hideo Sato; Seiji Horie; Nobuyoshi Sekikawa; Hisatake Ono, all of Asaka, Japan

[73] Assignee: Fuji Photo Film Co., Ltd., Minami Ashigara, Japan

[21] Appl. No.: 707,737

[22] Filed: Jul. 21, 1976

[30] Foreign Application Priority Data

Jul. 21, 1975 Japan .................................. 50-89009

[51] Int. Cl.² .......................................... C07D 237/32
[52] U.S. Cl. .................................. 544/237; 424/250
[58] Field of Search .................................. 260/250 P

[56] References Cited

U.S. PATENT DOCUMENTS

| | | | |
|---|---|---|---|
| 3,429,882 | 2/1969 | Doebel et al. | 260/250 P |
| 3,479,355 | 11/1969 | Doebel et al. | 260/250 P |
| 3,882,119 | 5/1975 | Nathansohn et al. | 260/250 P |

Primary Examiner—Nicholas S. Rizzo
Attorney, Agent, or Firm—Sughrue, Rothwell, Mion, Zinn and Macpeak

[57] ABSTRACT

1-phthalazinone and 1-phthalazinone derivatives of the following formula:

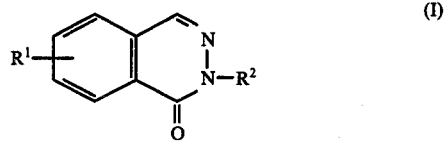

(I)

wherein $R^1$ represents a hydrogen atom, an alkyl group, an aralkyl group, an acyloxyl group, an alkoxyl group, a halogen atom, a nitro group, an amino group or an amido group; and $R^2$ represents a hydrogen atom, an alkyl group or an aryl group. Such can be prepared at good yields by the reaction of a benzoic acid derivative of the following formula:

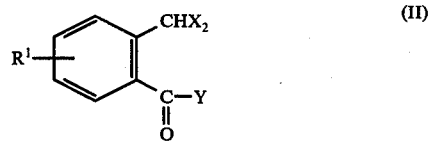

(II)

wherein $R^1$ has the same meanings as defined above; X represents a halogen atom; and Y represents a hydroxyl group, an alkoxyl group or a halogen atom; with hydrazine or a hydrazine derivative of the following formula:

$$R^2 - NH - NH_2 \qquad \text{(III)}$$

wherein $R^2$ has the same meanings as defined above.

20 Claims, No Drawings

PROCESS FOR PRODUCING PHTHALAZINONE AND DERIVATIVES OF THE SAME

BACKGROUND OF THE INVENTION

1. Field of the Invention

The present invention relates to a process for producing 1-phthalazinone and its derivatives, more particularly, to a process for producing 1-phthalazinone and its derivatives by the reaction of a benzoic acid derivative with hydrazine or a derivative thereof.

2. Description of the Prior Art 1-phthalazinone and its derivatives have been prepared by the reaction of o-formylbenzoic acid, which is derived from phthalic anhydride via several reaction steps, with hydrazine or a derivative thereof as described in P.R. Austin, E.W. Bousquet and W.A. Lazier, J. Am. Chem. Soc., 59, 864 (1937); R.L. Shriner and F.J. Wolff, Org. Synth., 23, 74 (1943); and C. Liebermann and A. Bistrzycki, Ber. Deut. Chem. Ges., 26, 531 (1893). This method of preparation, however, is disadvantageous in cost due to the multiplicity of reaction steps and the limited industrial uses of o-formylbenzoic acid.

1-phthalazinone and its derivatives have also been prepared from naphthalene, which is a less expensive starting material, via an oxidation using potassium permanganate. In this method, however, there is used an aqueous alkaline solution of potassium permanganate, the use of which involves the possibility of environmental pollution and hence requires the use of apparatus equipped to reduce discharged pollutants, which results in the use of intricate apparatus and production procedures.

Of 1-phthalazinone derivatives, those having substituent groups on the benzene ring have been prepared by other complicated processes since they are incapable of being prepared by the above processes.

SUMMARY OF THE INVENTION

It is therefore one object of this invention to provide a process for producing 1-phthalazinone and its derivatives, which process is capable of producing them at a high yield from readily available materials via fewer reaction steps.

Another object of the invention is to provide a process for producing 1-phthalazinone and its derivatives, which process has a reduced possibility of causing environmental pollution.

Still another object of the invention is to provide a process for producing 1-phthalazinone and its derivatives having various substituent groups, which process is capable of producing them at a high yield via fewer and similar reaction steps, irrespective of the kind of substituent groups.

According to the invention, there is provided a process for producing 1-phthalazinone and its derivatives represented by the following general formula:

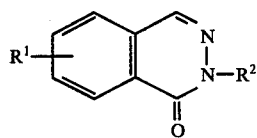
(I)

wherein $R^1$ represents a hydrogen atom, an alkyl group, an aralkyl group, an acyloxyl group, an alkoxyl group, a halogen atom, a nitro group, an amino group or an amido group; preferred $R^1$ groups include a hydrogen atom; an alkyl group having 1 – 12 carbon atoms; an aralkyl group which is a $C_1$ to $C_{12}$ carbon atom alkyl group substituted with a phenyl group; an acyloxyl group having 1 – 12 carbon atoms, which can be substituted with a phenyl group if desired; an alkoxy group having 1 – 12 carbon atoms which can be substituted with a phenyl group, if desired; halogen; nitro; amino ($-NH_2$) or amino substitued with 1 or 2 alkyl groups having 1 – 12 carbon atoms, an aralkyl group as above defined, or a phenyl group; and an amido group substituted with an alkyl group having 1 – 12 carbon atoms or substituted with a phenyl group which may, if desired, itself be substituted with an alkyl group having 1 – 4 carbon atoms; and $R^2$ represents a hydrogen atom, an alkyl group or an aryl group; which comprises reacting a benzoic acid derivative represented by the following general formula:

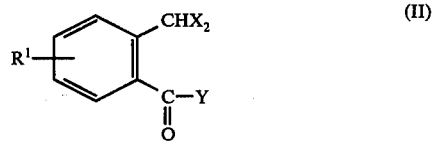
(II)

wherein $R^1$ has the same meanings as defined above; X represents a halogen atom; and Y represents a hydroxyl group, an alkoxyl group or a halogen atom; with hydrazine or its derivative represented by the following general formula:

$$R^2 - NH - NH_2 \qquad (III)$$

wherein $R^2$ has the same meanings as defined above.

DETAILED DESCRIPTION OF THE INVENTION

As examples of substituent groups in the compounds represented by the above general formulae, mention may be made of the following.

Alkyl groups shown by $R^1$: methyl, ethyl, propyl, butyl, pentyl, isopropyl, isobutyl, sec-butyl, t-butyl, and the like; acyloxyl groups shown by $R^1$: acetoxyl, propionyloxyl, benzoyloxyl, toluoyloxyl, and the like; alkoxyl groups shown by $R^1$: methoxyl, ethoxyl, propoxyl, isopropoxyl, butoxyl, t-butoxyl, pentyloxyl, cyclohexyloxyl, benzyloxyl, phenethyloxyl, and the like; halogen atoms shown by $R^1$: fluorine, chlorine, bromine and iodine; amino groups shown by $R^1$: amino, methylamino, ethylamino, propylamino, isopropylamino, butylamino, pentylamino, benzylamino, phenethylamino, dimethylamino, diethylamino, methylpropylamino, and the like; amido groups shown by $R^1$: acetoamido, propionmido, butyramido, valeramido, pivalamido, benzamide, toluamido, and the like.

Alkyl groups shown by $R^2$: the same alkyl groups as in $R^1$ above including an aralkyl group which is a alkyl group (having 1 to 12 carbon atoms) substituted with a phenyl group; aryl groups shown by $R^2$ include aryl groups which may be substituted with an alkyl group having 1 to 4 carbon atoms, a halogen atom, a nitro group, an amino group ($-NH_2$ group), an alkoxyl group having 1 to 4 carbon atoms, and the like: phenyl, tolyl, xylyl, nitrophenyl, aminophenyl, chlorophenyl, bromophenyl, methoxyphenyl, ethoxyphenyl, and the like;

Halogen atoms shown by X: chlorine, bromine and iodine;

Alkoxyl groups shown by Y: preferably alkoxyl groups having 1 to 4 carbon atoms, e.g., methoxyl, ethoxyl, propoxyl, isopropoxyl, and the like; and halogen atoms shown by Y: chlorine, bromine and iodine. Y is preferably an alkoxyl group as mentioned above.

Preferred sub-classes within the above grouping are those (1) wherein $R^1$ is hydrogen, alkyl or aralkyl, $R^2$ is as recited and Y is hydroxyl; (2) a class identical to (1) except Y is alkoxyl; (3) a class identical to (1) except Y is halogen; classes as in (1) - (3) except $R^1$ is acyloxy or alkoxyl; classes as in (1) - (3) except $R^1$ is halogen; classes as in (1) - (3) except $R^1$ is nitro; classes as in (1) - (3) except $R^1$ is amino; classes as in (1) - (3) except $R^1$ is amido.

Typical and favorable examples of benzoic acid derivatives shown by the above Formula (II) include α,α-dichloroo-toluic acid and its methyl and ethyl esters, α,α-dibromoo-toluic acid and its methyl and ethyl esters, 2-dichloromethyl-3-nitrobenzoic acid and its methyl and ethyl esters, 2-dibromomethyl-3-nitrobenzoic acid and its methyl and ethyl esters, 2-dichloromethyl-3-methoxybenzoic acid and its methyl and ethyl esters, 2-bromomethyl-5-ethoxybenzoic acid and its methyl and ethyl esters, 2-dichloromethyl-4-chlorobenzoic acid and its methyl and ethyl esters, 2-dibromomethyl-4-bromobenzoic acid and its methyl and ethyl esters, and the like. Acid halides, such as acid chlorides and bromides, of the above described acids may also be used in the reaction of the invention, but they are liable to form a greater proportion of by-products. On the other hand, in cases where the above described derivatives of the free acid or ester type are used in the reaction of the invention, only slight amounts of by-products are formed.

Typical and favorable examples of compounds shown by Formula (III) include hydrazine, hydrazine hydrate, phenylhydrazine, benzylhydrazine, methylhydrazine, ethylhydrazine, and the like.

Typical examples of 1-phthalazinone derivatives prepared by the process of the invention include 1-phthalazinone, 2-methyl-1-phthalazinone, 2-ethyl-1-phthalazinone, 2-phenyl-1-phthalazinone, 2-benzyl-1-phthalazinone, 6-chloro-1-phthalazinone, 6-chloro-2-methyl-1-phthalazinone, 6-chloro-2-phenyl-1-phthalazinone, 5-nitro-1-phthalazinone, 5-nitro-2-ethyl-1-phthalazinone, 5-nitro-2-benzyl-1-phthalazinone, 7-ethoxy-1-phthalazinone, 7-methoxy-2-phenyl-1-phthalazinone, 6-bromo-1-phthalazinone, 6-chloro-2-ethyl-1-phthalazinone, and the like.

The reaction of the invention may be represented by the following reaction scheme:

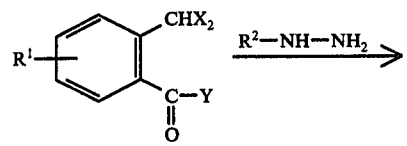

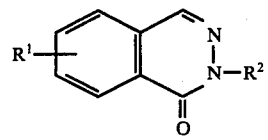

Compounds shown by Formula (II) which are used in the invention may be prepared by the processes described in E.L. Eliel and D.E. Rivard, J. Org. Chem., 17, 1252 (1952); and L. Reichel and W. Hampel, Z. Chem., 3, 190 (1963); or a suitable modification thereof.

In practicing the reaction of the invention, a benzoic acid derivative shown by Formula (II) is allowed to react with an equimolar or more than equimolar amount of hydrazine or its derivative shown by Formula (III) in a solvent in the presence of a base. As solvents for the reaction, there may be used a variety of conventional organic solvents, preferably polar solvents, including alcohols such as methanol, ethanol, propanol, etc., acetonitrile, formamide, dimethylformamide, dimethylsulfoxide, benzene, tetrahydrofuran, dioxane, chloroform, and the like. Of these solvents, methanol, ethanol, acetonitrile, formamide, dimethylformamide, and dimethylsulfoxide are particularly preferable. If desired, mixtures of these solvents may also be used. The amount of solvent is generally that to dissolve all reaction components and to permit easy mixing.

The base is utilized as a dehydrohalogenating agent (which is theoretically consumed in more than double the equimolar quantity of the benzoic acid derivative), but, when used in large excess, the hydrazine or its derivative can serve as a dehydrohalogenating agent. Useful bases include inorganic bases and organic bases. Examples of useful inorganic bases include carbonates such as $Na_2CO_3$, $NaHCO_3$, $K_2CO_3$, $KHCO_3$, and the like. As examples of organic bases, there may be used primary ($RNH_2$), secondary ($R_2NH$) and tertiary ($R_3N$) amines, wherein examples of R groups are alkyl groups having 1- 12 carbon atoms aralkyl groups having 7 - 10 carbon atoms, a phenyl group and the like, pyridine, N-alkyl piperidines (wherein the alkyl moiety preferably has 1 - 12 carbon atoms) and the like. Most preferred for use as the organic bases are tertiary amines, such as dimethylaniline, diethylaniline, triethylamine, N-alkylpiperidines as defined and pyridine. In the case where acetonitrile is used as a solvent, no dehydrohalogenating agent is required.

The reaction time may be varied according to other reaction conditions, but is is ordinarily from about 1 hour to about 4 hours. The product can be isolated and purified by conventional methods.

It is well knonw that 1-phthalazinone and 1-phthaladinone derivatives are useful as a color toning agent for heat-developable light-sensitive materials as are described in U.S. Pats. No. 3,457,075; 3,492,706; 3,909,271, etc. The products of this invention find use therein.

These heat-developable light-sensitive materials consist essentially of a silver salt of a long chain fatty acid, a reducing agent, and a catalytic amount of light-sensitive silver halide (which is a catalyst for the oxidation-reduction image forming reaction of the silver salt of the fatty acid and the reducing agent under heating).

1-phthalazinone and/or 1-phthalazinone derivative provide a dark tone to the above images, especially a black tone. The amount of toning agent is comveniently from about $1 \times 10^{-4}$ mol to about 2 mols per mol of the silver salt of the fatty acid.

The heretofore offered disclosure will enable one skilled in the art to practice the present invention with ease. However, as with most process inventions contemplated as useful for commerical scale operation, certain highly preferred conditions do exist, which are discussed below. It should be understood, however, that the conditions set forth below are not limitative.

It is preferred that the amount of hydrazine derivative (III) be not less than one mol, even more preferably 3–4 moles, per mol of the benzoic acid derivative (II). While practicing in the above range, the amount of base is preferably not less than about 2 moles, even more preferably 3–4 moles, per mol of the benzoic acid derivative (II). The reaction is conveniently performed at atmospheric pressure and at a temperature of from ordinary room temperature to about 200° C in a period of from about 1 hour to about 4 hours. The amount of solvent used is not important, and generally, when such is used, is merely sufficient to dissolve all reactants and ease mixing.

The invention is illustrated in further detail by the following examples, all at 1 atm. unless otherwise stated.

EXAMPLE 1

A solution of 29.4 g (0.1 mole) of α,α-dibromo-o-toluic acid and 16 g (0.32 mole) of hydrazine hydrate in 200 ml of ethanol was heated under reflux with stirring for 1 hour. The solvent was evaporated under reduced pressure, and the residue recrystallized from ethanol to give 12.8 g (yield: 88%) of 1-phthalazinone having a melting point of 181°–182° C.

Analysis — Calcd. for $C_8H_6N_2O$ (percent): C, 65.75; H, 4.11; N, 19.18. Found (percent): C, 65.78; H, 4.21; N, 19.11.

EXAMPLE 2

Example 1 was repeated, except that 11 g (0.22 mole) of hydrazine hydrate was used, 22.3 g (0.22 mole) of triethylamine was additionally used as a dehydrohalogenating agent, and the heating was carried out for 2 hours. There was obtained 11.4 g (yield: 78%) of 1-phthalazinone having a melting point of 181°–182° C.

EXAMPLE 3

A solution of 23.9 g (0.1 mole) of 4-chloro-2-dichloromethylbenzoic acid and 16 g (0.32 mole) of hydrazine hydrate in 200 ml of ethanol was heated under reflux for 3 hours. The ethanol was evaporated under reduced pressure, and the residue recrystallized from ethanol to give 11.4 g (yield: 63%) of 6-chloro-1-phthalazinone having a melting point of 272°–273° C.

Analysis — Calcd. for $C_8H_5N_2OCl$ (percent): C, 53.21; H, 2.79; N, 15.50. Found (percent): C, 53.14; H, 2.85; N, 15.76.

EXAMPLE 4

A solution of 29.4 g (0.1 mole) of α,α-dibromomethyl-o-toluic acid and 14.7 g (0.32 mole) of methylhydrazine in 100 ml of ethanol was heated under reflux for 3 hours. The solvent was evaporated under reduced pressure, and the residue recrystalized from ethanol to give 12.0 g (yield: 75%) of 2-methyl-1-phthalazinone having a melting point of 111°–112° C.

Analysis — Calcd. for $C_9H_8N_2O$ (percent): C, 67.50; H, 5.00; N, 17.50. Found (percent): C, 67.50; H, 5.15; N, 17.62.

EXAMPLE 5

α,α-dibromo-o-toluic acid (29.4 g), benzylhydrazine dihydrochloride (19.5 g) and triethylamine (60 g) were allowed to react as in Example 4. There was obtained 12.1 g (yield: 51%) of 2-benzyl-1-phthalazinone having a melting point of 104°–105° C.

Analysis — Calcd. for $C_{15}H_{12}N_2O$ (percent): C, 76.27; H, 5.08; N, 11.86. Found (percent): C, 76.18; H, 5.21; N, 12.03.

EXAMPLE 6

α,α-dibromo-o-toluic acid (29.4 g) and phenylhydrazine (34.6 g) were allowed to react as in Example 4. There was obtaoined 6.7 g (yield: 30%) of 2-phenyl-1-phthalazinone having a melting poin of 104°–105° C.

Analysis — Calcd. for $C_{14}H_{10}N_2O$ (percent); C, 75.68; H, 4.50; N, 12.61. Found (percent): C, 75.47; H, 4.65; N, 12.60.

While the invention has been described in detail and with reference to specific embodiments thereof, it will be apparent to one skilled in the art that various changes and modifications can be made therein without departing from the spirit and scope thereof.

What is claimed is:

1. A process for producing a 1-phthalazinone represented by the following formula:

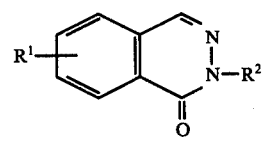

(I)

wherein
- $R^1$ represents a hydrogen atom; alkyl having 1 to 12 carbon atoms; aralkyl having a $C_1$ to $C_{12}$ carbon alkyl substituted with phenyl; acyloxyl having 1 to 12 carbon atoms which may be substituted with phenyl; alkoxyl having 1 to 12 carbon atoms which may be substituted with phenyl; a halogen atom; a nitro group; an amino group; or an amido group, and
- $R^2$ represents a hydrogen atom; alkyl having 1 to 12 carbon atoms; aralkyl having a $C_1$ to $C_{12}$ carbon alkyl substituted with phenyl; or phenyl which may be substituted with alkyl having 1 to 4 carbon atoms, a halogen atom, a nitro group, an amino group or alkoxyl having 1 to 4 carbon atoms; by reacting in an organic solvent a benzoic acid derivative represented by the following formula:

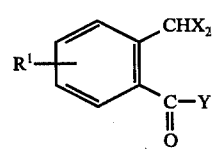

(II)

wherein $R^1$ has the same meanings as defined above; X represents a halogen atom; and Y represents hydroxyl; alkoxyl having 1 to 4 carbon atoms; or a halogen atom; with a hydrazine represented by the following formula:

$R^2-NH-NH_2$ (III)

wherein $R^2$ has the same meaning as defined above.

2. The process as claimed in claim 1, wherein said reaction is carried out in the presence of a base.

3. The process as claimed in claim 1, wherein said benzoic acid derivative is a compound selected from the group consisting of α,α-dichloro-o-toluic acid, α,α-dibromo-o-toluic acid, 2-dichloromethyl-3-nitrobenzoic acid, 2-dibromomethyl-3-nitrobenzoic acid, 2-dichloromethyl-3-methoxybenzoic acid, 2-dibromomethyl-5-ethoxybenzoic acid, 2-dichloromethyl-4-chlorobenzoic acid, 2-dibromomethyl-4-bromobenzoic acid, and methyl and ethyl esters thereof.

4. The process as claimed in claim 3, wherein said hydrazine is a compound selected from the group consisting of hydrazine, hydrazine hydrate, phenyl hydrazine, benzylhydrazine, methylhydrazine and ethylhydrazine.

5. The process as claimed in claim 4, wherein said 1-phthalazinone is a compound selected from the group consisting of 1-phthalazinone, 2-methyl-1-phthalazinone, 2-ethyl-1-phthalazinone, 2-phenyl-1-phthalazinone, 2-benzyl-1-phthalazinone, 6-chloro-1-phthalazinone, 6-chloro-2-methyl-1-phthalazinone, 6-chloro-2-phenyl-1-phthalazinone, 5-nitro-1-phthalazinone, 5-nitro-2-ethyl-1-phthalazinone, 5-nitro-2-benzyl-1-phthalazinone, 7-ethoxyl-1-phthalazinone, 7-methoxy-2-phenyl-1-phthalazinone, 6-bromo-1-phthalazinone and 6-chloro-2-ethyl-1-phthalazinone.

6. The process as claimed in claim 5 wherein the amount of the hydrazine is not less than one mol per mol of the benzoic acid derivative.

7. The process of claim 6 wherein said reaction is conducted at from about room temperature to about 200° C for about 1 hour to 4 hours at atmospheric pressure.

8. The process of claim 2 wherein said base is used in an amount of not less than 2 moles per mol of the benzoic acid derivative.

9. The process as claimed in claim 1, wherein the amount of the hydrazine is 3 to 4 mols per mol of the benzoic acid derivative.

10. The process as claimed in claim 1, wherein said organic solvent is selected from the group consisting of an alcohol, acetonitrile, formamide, dimethylformamide, dimethylsulfoxide, benzene, tetrahydrofuran, dioxane or chloroform.

11. The process as claimed in claim 10, wherein said organic solvent is methanol, ethanol, acetonitrile, formamide, dimethylformamide or dimethylsulfoxide.

12. The process as claimed in claim 2, wherein said base is an organic base.

13. The process as claimed in claim 12, wherein said organic base is selected from the group consisting of
   (i) a primary amine of the formula $RNH_2$;
   (ii) a secondary amine of the formula $R_2NH$; or
   (iii) a tertiary amine of the formula $R_3N$, wherein R is alkyl of 1 to 12 carbon atoms, aralkyl of 7 to 10 carbon atoms or phenyl and wherein said tertiary amine can be pyridine or an N-alkyl piperidine, said alkyl of said N-alkyl piperidine having 1 to 12 carbon atoms.

14. The process as claimed in claim 13, wherein said organic base is a tertiary amine.

15. The process as claimed in claim 14, wherein said tertiary amine is selected from the group consisting of dimethylaniline, diethylaniline, an N-alkyl piperidine, pyridine or triethylamine.

16. The process as claimed in claim 1, wherein said organic solvent is acetonitrile.

17. The process as claimed in claim 1, wherein for $R^1$, said alkyl is selected from the group consisting of methyl, ethyl, propyl, butyl, pentyl, isopropyl, isobutyl, sec-butyl and t-butyl;

said acyloxyl is selected from the group consisting of acetoxyl, propionyloxyl, benzoyloxyl and toluoyloxyl;

said alkoxyl is selected from the group consisting of methoxyl, ethoxyl, propoxyl, isopropoxy, butoxyl, t-butoxyl, pentyloxyl, cyclohexyloxyl, benzyloxyl and phenethyloxyl;

said halogen is selected from the group consisting of fluorine, chlorine, bromine and iodine;

said amino is selected from the group consisting of amino, methylamino, ethylamino, propylamino, isopropylamino, butylamino, pentylamino, benzylamino, phenethylamino, dimethylamino, diethylamino and methylpropylamino; and said amido is selected from the group consisting of acetoamido, propionamide, butyramido, valeramido, pivalamido, benzamide and toluamido.

18. The process as claimed in claim 1, wherein for $R^2$, said alkyl is selected from the group consisting of methyl, ethyl, propyl, butyl, pentyl, isopropyl, isobutyl, sec-butyl and t-butyl; and said phenyl which may be substituted is selected from the group consisting of phenyl, tolyl, xylyl, nitrophenyl, aminophenyl, chlorophenyl, bromophenyl, methoxyphenyl and ethoxy phenyl.

19. The process as claimed in claim 1, wherein X represents chlorine, bromine or iodine.

20. The process as claimed in claim 1, wherein for Y, said alkoxyl is selected from the group consisting of methoxyl, ethoxyl, propoxyl or isopropoxyl; and said halogen is selected from the group consisting of chlorine bromine and iodine.

* * * * *